United States Patent
Porter et al.

(10) Patent No.: US 8,168,845 B2
(45) Date of Patent: May 1, 2012

(54) SEPARATION PROCESS

(75) Inventors: John R. Porter, Friendswood, TX (US);
Dana L. Pilliod, League City, TX (US)

(73) Assignee: ExxonMobil Chemical Patents Inc.,
Houston, TX (US)

( * ) Notice: Subject to any disclaimer, the term of this patent is extended or adjusted under 35 U.S.C. 154(b) by 265 days.

(21) Appl. No.: 12/604,836

(22) Filed: Oct. 23, 2009

(65) Prior Publication Data

US 2010/0125163 A1 May 20, 2010

Related U.S. Application Data

(60) Provisional application No. 61/116,097, filed on Nov. 19, 2008.

(51) Int. Cl.
*C07C 7/12* (2006.01)

(52) U.S. Cl. ......... 585/828; 585/820; 585/825; 585/827

(58) Field of Classification Search ................ None
See application file for complete search history.

(56) References Cited

U.S. PATENT DOCUMENTS

| | | |
|---|---|---|
| 2,985,589 A | 5/1961 | Broughton et al. |
| 3,040,777 A | 6/1962 | Carson et al. |
| 3,192,954 A | 7/1965 | Gerhold et al. |
| 3,201,491 A | 8/1965 | Stine et al. |
| 3,291,726 A | 12/1966 | Broughton |
| 3,422,848 A | 1/1969 | Liebman et al. |
| 3,510,423 A | 5/1970 | Neuzil et al. |
| 3,686,342 A | 8/1972 | Neuzil |
| 3,706,812 A | 12/1972 | Derosset et al. |
| 4,029,717 A | 6/1977 | Healy et al. |
| 4,274,982 A | 6/1981 | Chu |
| 4,434,051 A | 2/1984 | Golem |
| 4,851,604 A | 7/1989 | Absil et al. |
| 5,365,003 A | 11/1994 | Chang et al. |
| 5,470,464 A | 11/1995 | Priegnitz |
| 5,498,822 A | 3/1996 | Eccli et al. |
| 5,750,820 A | 5/1998 | Wei |
| 5,912,395 A | 6/1999 | Noe |
| 7,208,651 B2 | 4/2007 | Frey |
| 2005/0222482 A1 | 10/2005 | Lee et al. |
| 2008/0036913 A1 | 2/2008 | Yeh et al. |
| 2008/0149565 A1 | 6/2008 | Lee et al. |

FOREIGN PATENT DOCUMENTS

WO WO 03/026772 4/2003

OTHER PUBLICATIONS

C.W. Chi et al. "Adsorptive Separation (Liquids)," Kirk-othmer Encyclopedia of Chemical Technology, $3^{rd}$ Ed. (1978), vol. 1, pp. 563-581.
D.B. Broughton et al., "Fundamentals of Adsorption", Schloss Elmau, Upper Bavaria, Germany, May 6-11, 1983, pp. 115-124.
D.B. Broughton et al., "The Parex Process for Recovering Paraxylene," Chemical Engineering Progress, Sep. 1970, vol. 66, No. 9, pp. 70-76.
Meyers' Handbook of Petroleum Refining Processes, $3^{rd}$ Ed. (2004), McGraw-Hill Handbooks, pp. 2.51.

*Primary Examiner* — Tam M Nguyen
(74) *Attorney, Agent, or Firm* — Andrew B. Griffis

(57) ABSTRACT

The invention relates to an improved absorption-type separation and/or purification processes having dual rotary valves.

9 Claims, 3 Drawing Sheets

SEPARATION PROCESS

CROSS-REFERENCE TO RELATED APPLICATIONS

This application claims priority to U.S. Provisional Application No. 61/116,097, filed Nov. 19, 2008, which is incorporated herein by reference.

FIELD OF THE INVENTION

The invention relates to absorption-type separation and/or purification processes.

BACKGROUND OF THE INVENTION

Adsorption from the liquid phase has long been used for removal of contaminants present at low concentrations in process streams. The commercial use of adsorption for the recovery of major components of feed streams as pure products, sometimes termed bulk separations, is a comparatively recent development.

Examples of bulk separation include the separation of linear paraffins from branched-chain cyclic hydrocarbons, separation of olefins from paraffins, and the separation of C8 aromatic isomers, which include xylenes and ethylbenzene. Typically these processes use zeolitic adsorbents because of the particularly useful selectivities developed, but the technology and theory are equally applicable to suitably selective nonsieve adsorbents such as alumina, charcoal, metal oxides, and so on.

Development of large-scale bulk separations from the liquid phase has been accomplished by the use of a flow scheme simulating the continuous countercurrent flow of absorbent and process liquid, without actual movement of the adsorbent ("simulated moving bed" or SMB). See, for instance, U.S. Pat. No. 2,985,589, and Kirk-Othmer Encyclopedia of Chemical Technology, Third Edition (1978), Vol. 1, page 563-581). Such processes have been developed for the separation of p-xylene from a mixture of C8 aromatics (UOP Parex™), n-paraffin separation (UOP Molex™), olefin-paraffin separation (UOP Olex™). Variants have been developed, such as the Toray Aromax™ process for p-xylene separation. Each these products have important and well-known uses, e.g., p-xylene for the production of polyester fibers and plastics.

SMB have recently also been used for separation on a smaller scale, such as for separating pharmaceuticals, biochemicals, and fragrances. By way of example, see WO 2003026772.

In essentially all of these adsorptive separation units using a simulated countercurrent movement of the adsorbent and the feedstream, the simulation involves holding the adsorbent in place in one or more cylindrical adsorbent chambers. The positions at which the streams involved in the process enter and leave the chambers are slowly shifted along the length of the beds by means of, for example, a rotary valve, which functions on the same principle as a multi-port stopcock. Normally there are at least four streams (feed, desorbent, extract and raffinate) employed in this procedure and the location at which the feed and desorbent streams enter the chamber and the extract and raffinate streams leave the chamber are simultaneously shifted in the same direction at set intervals. Each shift in location of these transfer points delivers or removes liquid from a different bed within the chamber. For p-xylene separations, the extract stream is composed of p-xylene and desorbent and the raffinate stream is composed of desorbent and the p-xylene-depleted xylene mixture.

This shifting could be performed using a dedicated line for each stream at the entrance to each bed. However, this would greatly increase the cost of the process and therefore the lines are reused and each line carries one of the four process streams at some point in the cycle. In SMB, the feedstream is connected to a series of beds in sequence, first to bed no. 1, then to bed no. 2, and so forth for numerous beds, generally being between 12 and 24. These beds may be considered to be portions of a single large bed whose movement is simulated. Each time the feedstream destination is changed, it is also necessary to change the destinations (or origins) of at least three other steams, which may be streams entering the beds, such as the feedstream, or leaving the beds, such as the extract and raffinate. Desorbent and various flushes may also enter and leave the beds. The moving bed simulation may be simply described as dividing the bed into series of fixed beds and moving the points of introducing and withdrawing liquid steams past the series of fixed beds instead of moving the beds past the introduction and withdrawal points. See U.S. Patent Application 2008036913.

The general technique employed in the performance of SMB technology is well described in the literature. For instance a general description directed to the recovery of p-xylene was presented at page 70 of the September 1970 edition of Chemical Engineering Progress (Vol. 66, No 9). A generalized description of the process with an emphasis on mathematical modeling was given at the International Conference on "Fundamentals of Adsorption", Schloss Elmau, Upper Bavaria, Germany on May 6-11, 1983 by D. B. Broughton and S. A. Gembicki. U.S. Pat. No. 4,029,717 issued to F. J. Healy et al., describes a SMB process for the recovery of p-xylene from a mixture of xylene isomers. Numerous other available references describe many of the mechanical parts of an SMB system, including rotary valves for distributing various liquid flows, the internals of the adsorbent chambers and control systems, e.g., see Kirk-Othmer Encyclopedia of Chemical Technology, Third Edition (1978), Vol. 1, previously cited, especially p. 569 et. seq.; and FIG. 4 therein; FIG. 2.6.4 in Meyers' Handbook of Petroleum Refining Processes (3rd Edition (2004), McGraw-Hill Handbooks, pg. 2.51).

With regard to the rotary valve, U.S. Pat. No. 2,985,589 describes the idea of moving ports on fixed beds and an accompanying rotary valve to distribute stream flows among the fixed beds. See also U.S. Pat. Nos. 3,040,777; 3,192,954; 3,422,848. Processes utilizing a rotary valve in an SMB process are described in numerous such as U.S. Pat. Nos. 3,201, 491 and 3,291,726. In U.S. Pat. No. 3,706,812, columns are linked together through tees connected to rotary valves, as shown in FIG. 1 of the patent. The disclosed system incorporated a check valve between each column and its tee to maintain correct directional flow. The patent also disclosed the use of solenoid valves to move the ports through the columns. A rotary valve as used in SMB may be described as accomplishing the simultaneous interconnection of at two separate groups of conduits.

The cyclical advancement of the streams through the solids may also be accomplished by utilizing a manifold arrangement to cause the fluid to flow in a counter current manner with respect to the solids. The valves in the manifold may be operated in a sequential manner to effect the shifting of the steams in the same direction as overall fluid flow throughout the adsorbent solids. See U.S. Pat. No. 3,706,812.

UOP Sorbex™ Processes, which include the Parex™, Molex™, and Olex™ processes described above, makes use of a rotary valve that typically distributes net in streams (feed and desorbent), net out streams (extract and raffinate), and assorted flushes (primary flush in, secondary flush in and flush out) to and from the appropriate sieve beds inside the sieve chambers in the SMB unit. The net in, net out and assorted flush streams are sequentially cycled through the various bed lines. The assorted flush streams are necessary to avoid contamination caused by the sharing of the bed lines from the other net in and net out streams. Sorbex™ Process units typically process several streams that have significantly different compositions. While the terms extract and raffinate are relative terms depending on the nature of the components being separated, the preference of the solids, and the nature of the apparatus or system, as used herein the term "extract" will mean a stream comprising product and desorbent and the term "raffinate" will mean a stream comprising by-products and desorbent.

The use of SMB is important for the separation of xylenes and especially p-xylene from a mixture of xylenes and ethylbenzene. See U.S. Pat. No. 3,686,342 and U.S. Pat. No. 3,510,423. Parex™ Process units, which make use of the rotary valve in the aforementioned SMB process, typically can be fed mixtures of xylenes of various concentrations, e.g., equilibrium xylenes, a concentrated p-xylene stream from a selective toluene disproportionation unit, filtrate from a crystallizer which is low in p-xylene concentration, and mixtures thereof. In the conventional configuration, all of the feedstreams are mixed together and sent to a rotary valve as one feed. As taught in U.S. Pat. No. 5,750,820, feedstreams may be kept separate and fed to different beds based their composition.

Numerous methods have been devised to increase the efficiency and/or productivity of the rotary valve in combination with adsorptive separation processes, such as taught in U.S. Pat. Nos. 4,434,051; 5,470,464; 5,750,820; 5,912,395; 7,208,651; U.S. Patent Applications 20060848065 and 20080149565.

However, with the necessity of increasing sources of feed streams used in a refinery and/or chemical plant, there is still a need for a system that can process a variety of feed sources at the same time without major increases in expensive new apparatus and/or without loss of efficiency. By way of example, there is the need to integrate new feedstreams having differing compositions, for instance feedstreams having higher concentrations of p-xylenes than equilibrium provided by a mixture of xylenes, such as provided by the Mobil Selective Toluene Disproportionation (STDP™) or Mobil Toluene to P-xylene (MTPX™) processes, providing feedstreams having >90 wt % p-xylene (see U.S. Pat. Nos. 4,274,982; 4,851,604; 5,365,003; 5,498,822), with xylene feedstreams having the equilibrium concentration of about 23 wt % para-xylene, and/or feedstreams having very low amount (about 3-6 wt %) of para-xylene, such as provided by crystallizer filtrate. Mixing the feedstreams is inefficient since at least one of the feedstreams is caused to have a decreased concentration of the desired extract. In addition, in current practice at least some of the bedlines and or beds are not in use at any given time, which is inefficient use of a very expensive resource.

The present inventors have surprisingly discovered that by providing parallel rotary valves configured or plumbed to operate independently provide, in embodiments, increased capability for additional feed and flush streams, which in embodiments substantially results in either increasing the capacity of a unit or decrease the energy requirement of a unit at constant capacity. This allows the designer and/or operator to optimize multiple feed locations, maintain or increase the number of flushes, such as to flush raffinate from the bed lines and flush desorbent into the sieve chambers between the raffinate and desorbent.

SUMMARY OF THE INVENTION

The invention is directed to parallel distributive valves, preferably rotary valves, configured or plumbed to operate independently in an SMB system. In embodiments, the system comprises at least two rotary valves having crossover piping configured or plumbed differently within each rotary valve so that two separate feeds, one to each rotary valve, may be utilized simultaneously or step-wise within the simulated moving bed absorptive separation system.

In embodiments, the invention also concerns a process of using the SMB system according to the invention, comprising the use of two separate feeds in an SMB system having parallel distributive valves.

In a preferred embodiment, the process comprises the purification of plural feedstreams within an SMB system without the necessity of merging feedstreams.

In another preferred embodiment, the feedstreams comprises at least two selected from equilibrium xylenes (about 23 wt %), a concentrated p-xylene stream from a selective toluene disproportionation unit (>90 wt %) and filtrate from a crystallizer which is low in p-xylene concentration (<10 wt %).

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

in FIG. 1, the two feeds to the process can be fed independently to each rotary valve without losing any feed flushing capability;

in FIG. 2, one rotary valve is configured to flush raffinate out of the bed lines and a second rotary valve is configured to use the raffinate flush out to flush desorbent back into the sieve chambers;

in FIG. 3, combining some of the features of FIGS. 1 and 2, the number of feeds and flushes can both be increased.

DETAILED DESCRIPTION

According to the invention, an SMB system is provided with at least two distributive valves plumbed independently to allow for simultaneous processing of at least two different feedstreams.

In embodiments, as has been discovered by the present inventors, it is preferred to have parallel rotary valve systems configured or plumbed differently to optimize feed locations, flush raffinate from the bed lines and flush desorbent into the sieve chambers between the raffinate and desorbent. This can be accomplished by providing the capability for more than one feed location while actually maintaining or increasing the number of flushes in SMB process such as in a Sorbex™ Process.

The invention may be better understood by referring to the several drawings. It will be understood that the following description is merely by way of example and that the invention may be practiced otherwise than as specifically set forth herein.

Figure 1:
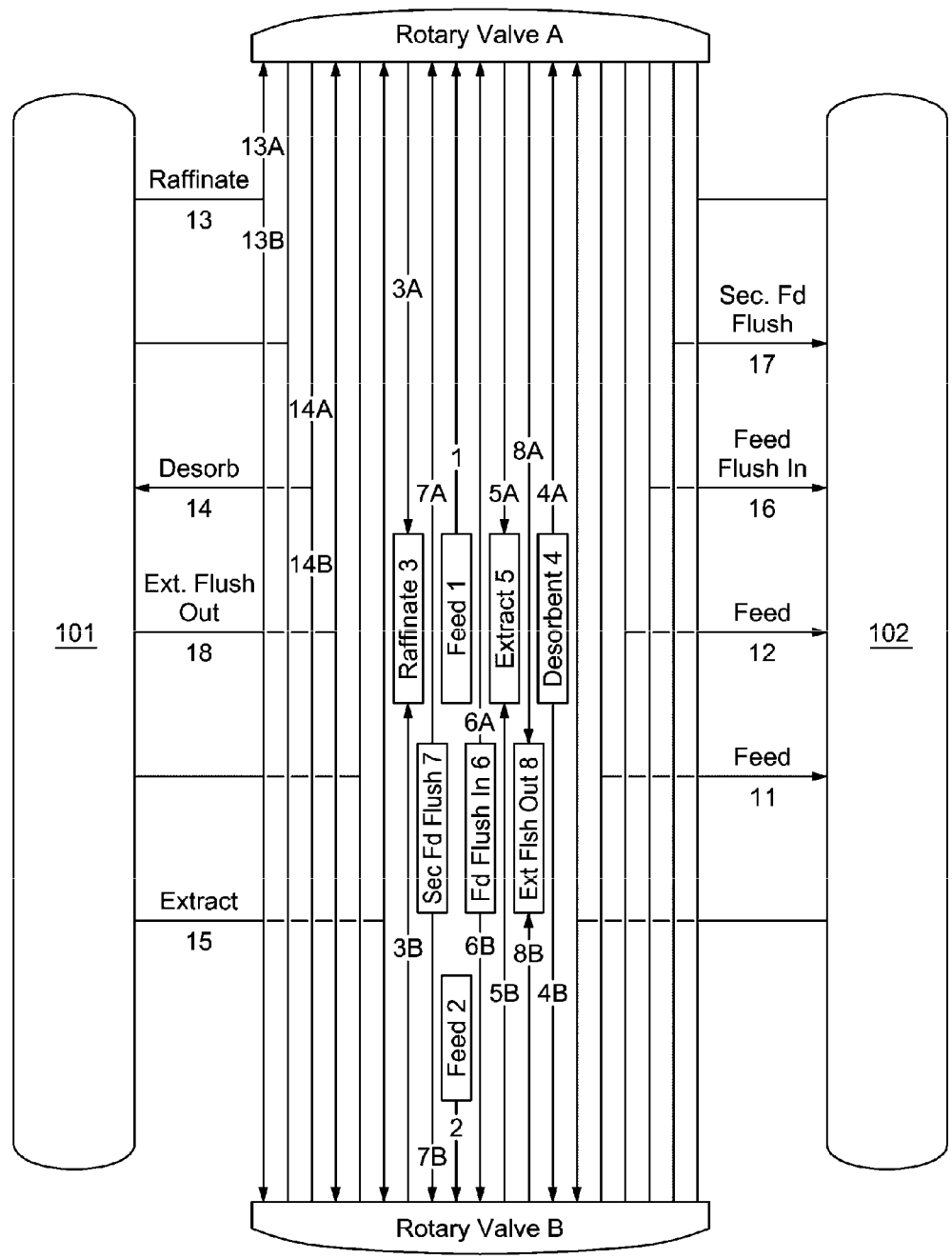
FIGS. 1-3 illustrate schematically embodiments of the present invention with respect to a SMB system, such as a Sorbex™ Process. More specifically, improvements provided by the present invention include, but are not limited to the following.

As shown in FIG. 1, in an embodiment, the two feeds, preferably two different feeds, which in embodiments may be feeds selected from the group consisting of (i) an equilibrium mixture of xylenes; (ii) a mixture of xylenes from a selective toluene disproportion unit having an amount of p-xylene greater than an equilibrium concentration; and (iii) and a mixture of xylenes from a crystallization process having an amount of p-xylene less than an equilibrium concentration, are fed independently to each rotary valve A and B through lines 1 and 2, respectively. There is no loss of feed flushing capability, since the second rotary valve B is configured (plumbed) differently from the first rotary valve A with respect to the bed lines. Throughout the several views the internal plumbing of the rotary valves is not shown because it is conventional per se with respect to each rotary valve. Parallel rotary valves A and B are configured independently to allow optimization of more than one feed. As depicted in the diagram, the three product streams (Raffinate 13, Extract 15 and Extract Flush Out 18) are withdrawn from the same location (sieve chamber 101).

In the example used for the system illustrated by the schematic in FIG. 1, the extract is a mixture of desorbent and p-xylene. The raffinate is a mixture of desorbent and p-xylene-depleted xylenes. Extract Flush Out is a mixture of desorbent and p-xylene. Each of these streams may, in more preferred embodiments, be purified downstream (not shown in the schematic) by, for instance, distillation, and the desorbent recycled to the system. Also in still another more preferred embodiments, the raffinate stream is sent to an isomerization unit (also not shown in the schematic but per se well known in the art) and then may also be recycled as a feedstream in the case where the feedstream to rotary valve A or B is an equilibrium mixture of xylenes. These more preferred embodiments, which may be combined, could be readily plumbed by the ordinary artisan in the possession of the present invention.

The respective streams of Raffinate, Extract, and extract Flush Out (bed lines 13, 15, and 18) split (e.g., into 13A and 13B; other notations omitted on the figure for convenience of view) and flow through each rotary valve A and B before recombining (streams 3A, 3B; 5A, 5B; 8A and 8B; respectively), at the outlets, respectively, for each stream. The plumbing for the outlets to processing downstream, such as by distillation, recycle, and the like, as discussed elsewhere herein, are not shown in the figure for convenience of view but are per se conventional plumbing. Feed streams 4 (Desorbent), 6 (Feed Flush in) and 7 (Secondary Feed Flush) split equally (4A, 4B; 6A, 6B; 7A, 7B) through each rotary valve A and B and then recombine (streams 14A and 14B combine into 14); likewise the appropriate streams combine (other notations omitted for convenience of view) into streams 16 and 17 before entering the sieve chambers 101 and 102 as shown in FIG. 1.

The Desorbent is a component or mixture of components which has an affinity for the sieve which is similar to the component being separated. In the case of p-xylene separations, the desorbent is typically para-diethylbenzene (PDEB). The Feed Flush In is a stream which flushes out the "contaminants" (feed) which lie in the SMB process bed lines. In the case of p-xylene separations, this stream is either PDEB, p-xylene or recycled line Flush Out. The secondary feed flush provides additional bed line flushing closer to the bed line where extract is removed. In p-xylene separations, the secondary feed flush is typically PDEB.

In the prior art, normally a single feed stream, which is a blend of two or more streams, is also split equally through each rotary valve and recombined to a single feed location in the sieve chambers. However, as shown in FIG. 1, these feed streams (feed 1 and feed 2) can be fed individually from each rotary valve by streams 11 and 12 to one or both sieve chambers (illustrated in the embodiment of FIG. 1 by the single sieve chamber 102). The sieve chambers in all the figures may be conventional sieve chambers using conventional adsorbent materials, per se known to one of skill in the art.

As with a distillation tower, the optimum location of a given feed is a function of composition. The C8 aromatics feed to a SMB unit typically comes from a number of sources, e.g., reformate, transalkylation, toluene disproportionation, selective toluene disproportionation, xylene isomerization, filtrate from a p-xylene crystallizer, and so on. The composition of these feeds varies widely in p-xylene purity (e.g., from about 3 wt %, or about 6 wt %, or about 9 wt % to about 80 wt % or about 90 wt %, or about 92 wt %, or about 94 wt %) and also ethylbenzene content (e.g., from about 1 wt % to about 25 wt %), and the feed may be a mixture of xylenes and ethylbenzenes from different sources, so each C8 isomer may vary from in the feedstream from trace impurity level to 99 wt % or even higher. Ethylbenzene is most notable as it is typically the most difficult isomer to separate from p-xylene.

However, mixing of feedstreams having different concentrations is, generally, thermodynamically inefficient considering that one of the advantages of the present invention is that two disparate feedstreams having in common at least one final product of interest may be processed in an SMB system, without mixing, to derive a common extract comprising said final product of interest.

By way of example, and not intending to be limiting, the diverse feedstreams may be selected from refinery and/or chemical plant feedstreams, such as the C8 aromatics feed discussed above with respect to an SMB process such as the Parex™ Process, include paraffin and/or olefins feedstream.

Also, by way of example, the final product of interest may be p-xylene, o-xylene, m-xylene, ethylene benzene, or mixtures thereof, cumene, one or more paraffins, one or more olefins, fructose and the like.

There are numerous other embodiments of the present invention that will immediately become apparent to one of ordinary skill in the art in possession of the present specification.

A few other specific and preferred embodiments will be mentioned below.

Figure 2:
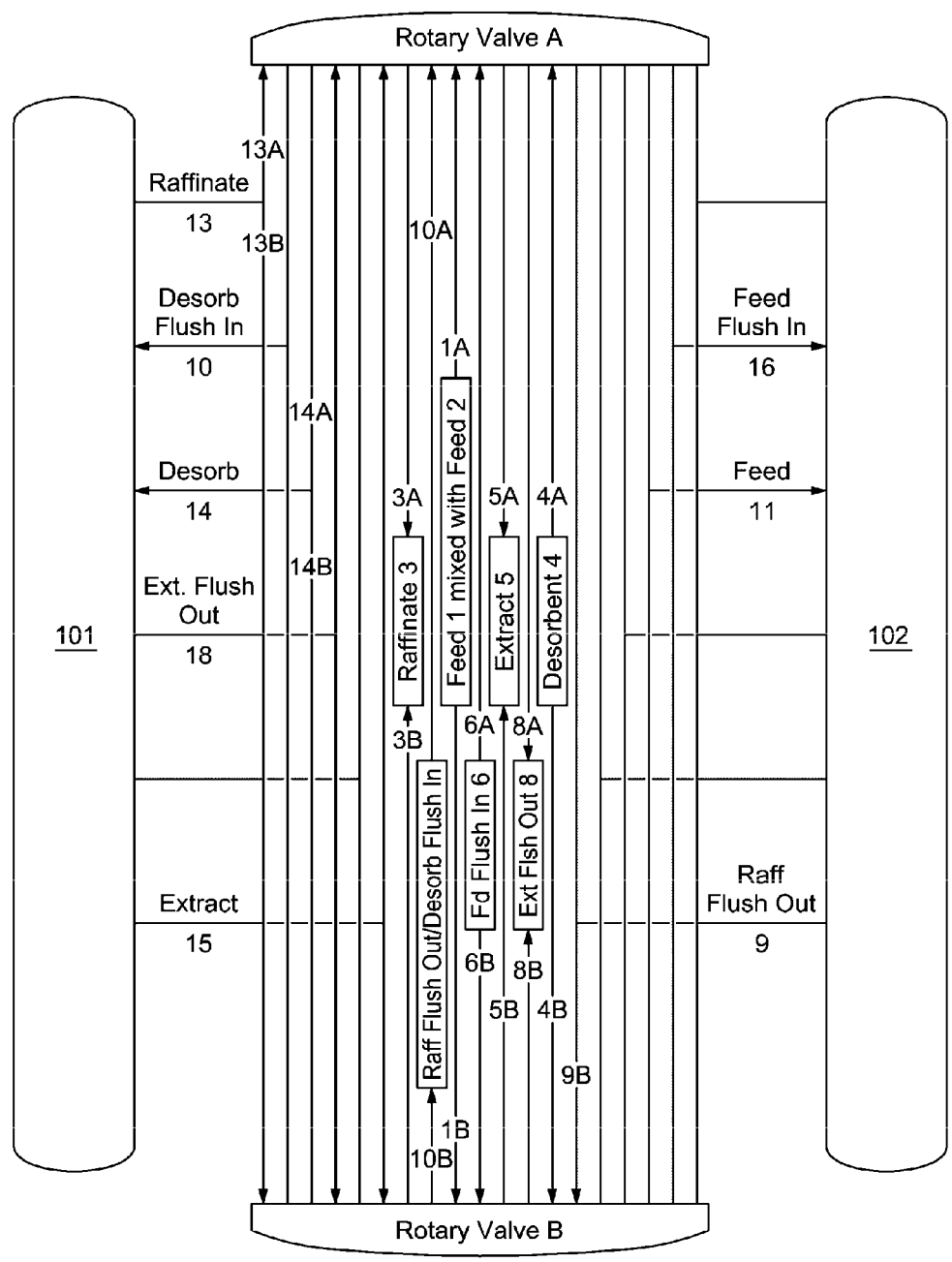

As shown in FIG. 2, in another embodiment, one rotary valve, A, is configured or plumbed to flush Raffinate out of the bed lines and the other rotary valve, B, is configured to use the Raffinate Flush Out to flush desorbent back into the sieve chambers. In FIG. 2, the parallel rotary valve configuration can also be utilized to increase the number of flushes in the SMB Process. The three product streams (Raffinate 13, Extract 15 and Extract Flush Out 18) are withdrawn from the same bed line for each rotary valve A and B. The streams split (e.g., as shown with respect to line 13, into lines 13A and 13B (other notations omitted for convenience of view) to 15 and 18 and flow through each rotary valve before recombining (3A, 3B; 5A, 5B; and 8A, 8B; respectively) at the outlet (streams indicated as Raffinate 3, Extract 5 and Flush Out 8). The streams may be sent downstream (plumbing not shown) for further processing, as discussed elsewhere herein, such as distillation followed by recycling. Feed streams of desorbent 4, feed flush in 6, and feed 1 split equally (4A, 4B; 6A, 6B;

1A, 1B, respectively) and pass through each rotary valve and then recombine (streams 14, 16 and 11) before entering the respective sieve chambers 101 and 102 (sieve chambers #1 and #2, respectively) at the same location. Stream 9 (Raffinate Flush Out) is routed through through bed line 10B to Rotary valve B and this same stream is used as stream 10 (desorbent flush in), which is routed through rotary valve A into a location between the raffinate withdrawal point 13 and the desorbent feed point 14. Stream 9, which in a preferred embodiment is a mixture of p-xylene depleted xylenes and paradiethylbenzene, will be displacing a bed line full of desorbent (paradiethylbenzene) back into the chamber. By doing so, the desorbent will be fully utilized in the SMB process. In preferred embodiments the rate of this flushing does not exceed the bed line volume/rotary valve stepping rate as this would introduce p-xylene depleted mixed xylenes into a location very close to the desorbent. This could result in contamination of the p-xylene product. In this configuration, the rotary valve tracks (internal plumbing of rotary valves; not shown since they are not per se an aspect of the present invention) in rotary valve A and B that are used for secondary feed flush in FIG. 1 are, as shown in FIG. 2, are now used for raffinate feed flush out 9 and desorbent feed flush in 16. Some debit for reduced feed flushing maybe realized, but the credits for raffinate and desorbent flushing would far outweigh any debit for reducing feed flushing.

Figure 3:
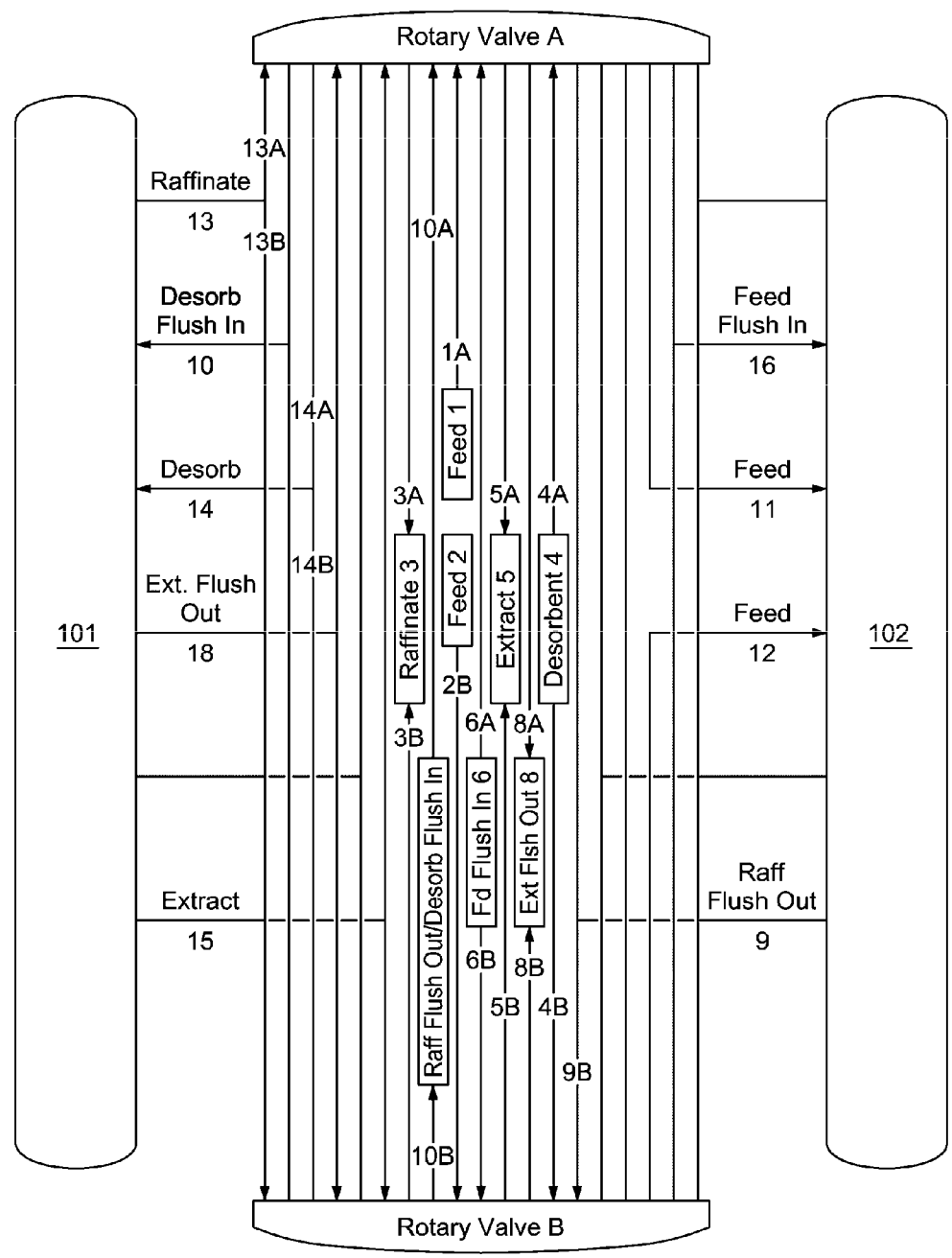

As shown in FIG. 3, in yet another embodiment, the number of feeds and flushes can both be increased.

The embodiment of the invention shown in FIG. 3 utilizes both feed optimization such as illustrated above in FIG. 1 and the optimized flushing as illustrated above in FIG. 2. In FIG. 3, Feeds 1 and 2 are fed by lines 1A and 2B, respectively, to rotary valves A and B, respectively, and then to different locations in sieve chamber 102 by streams 11 and 12. As depicted in the diagram, the three product streams (Raffinate 13, Extract 15 and Extract Flush Out 18) are withdrawn from the same location (bed line). The streams split (as in previous drawings, into 13A and 13B, and for the other streams 15 and 18 not separately marked for convenience of view) and flow through each rotary valve A and B before recombining by lines 3A, 3B; 5A, 5B, and 8A, 8B; respectively, at the outlet (streams 3, 5 and 8) which may then be further processed downstream, as discussed elsewhere in (lines for downstream processing not shown). Feed streams 4 (Desorbent) and 6 (Feed Flush in) split equally (4A, 4B; 6A, 6B; respectively) and pass through each rotary valve and then recombine (streams 14 and 16; 14A and 14B shown; similar lines for 16 not marked for convenience of view) before entering the sieve chambers 101 and 102, respectively, at the same location (bed lines). Stream 9 (Raffinate flush out) is routed through line 9B to Rotary valve B and this same stream is used as stream 10A (desorbent flush in), which is routed through rotary valve A into a location between the raffinate withdrawal point and the desorbent feed point. Stream 9, a mixture of p-xylene depleted xylenes and paradiethylbenzene, will be displacing a bed line full of desorbent (paradiethylbenzene) back into the chamber 102. Again, this more fully utilizes the desorbent in the SMB process. In preferred embodiments the rate of this flushing does not exceed the bed line volume/rotary valve stepping rate as this would introduce p-xylene depleted mixed xylenes into a location very close to the desorbent. This could result in contamination of the p-xylene product.

In another embodiment, the raffinate flush out can be routed through one rotary valve with the disposition of that stream being the raffinate tower feed. Instead of recycling raffinate flush out to desorbent flush in (as per FIG. 2), the second rotary valve can be plumbed to provide further (secondary) feed flushing capability.

Furthermore, an addition preferred embodiments would include increasing the number of raffinate and desorbent streams. Desorbent streams with different composition can be simultaneously fed to different points in the SMB process unit by plumbing the parallel rotary valves differently. The desorbent stream to the rotary valve is a mixture of desorbent which is separated in and recycled from the towers that fractionate the raffinate and extract. The composition of the desorbent from the raffinate tower is slightly different than the composition of the desorbent from the extract tower. The impurities in the desorbent from the raffinate tower are p-xylene-depleted C8 aromatics (predominantly o-xylene since it is the highest boiling C8 aromatic). The impurity in the desorbent from the extract tower is predominantly p-xylene. Thus in another preferred embodiment, the process further comprises feeding those streams independently into different points in the sieve beds. In addition, this optimization would allow relaxation of the tower specifications and reduction in energy input.

While the illustrative embodiments of the invention have been described with particularity, it will be understood that various other modifications will be apparent to and can be readily made by those skilled in the art without departing from the spirit and scope of the invention.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. The meanings of terms used herein shall take their ordinary meaning in the art; reference shall be taken, in particular, to Handbook of Petroleum Refining Processes, Third Edition, Robert A. Meyers, Editor, McGraw-Hill (2004).

What is claimed is:

1. A process for separating a first compound from a mixture comprising a first compound and at least one other compound in an SMB system, said process comprising the steps of:
   a. providing a first feedstream, having a first concentration of said first compound and a first concentration of a second compound, to a first distributive valve, said first distributive valve fluidly connected to a second distributive valve, and to a plurality of chambers comprising an adsorptive material selective for the adsorption of said first compound or said second compound;
   b. providing a second feedstream having a second concentration of said first compound, different from said first concentration of said first compound, and a second concentration of a second compound, to said second distributive valve, fluidly connect to said first distributive valve, and to at least one of said chambers comprising an adsorptive material;
   c. introducing said first feedstream into said at least one of said plurality of chambers comprising said adsorptive material and selectively adsorbing said first or said second compound on said adsorptive material to provide a modified adsorptive material and a modified first feedstream having a third concentration of said first compound, different from said first concentration of said first compound, and a third concentration of said second compound, different from said first concentration of said first compound, withdrawing said modified first feedstream from said at least one chamber, and passing said modified first feedstream to said first distributive valve, said second distributive valve, or a combination thereof;

d. introducing said second feedstream into said at least one of said plurality of chambers comprising said adsorptive material, and selectively adsorbing said first or said second compound on said adsorptive material to provide a modified adsorptive material and a modified second feedstream having a fourth concentration of said first compound, different from said second concentration of said first compound, and a fourth concentration of said second compound, different from said second concentration of said first compound, wherein said fourth concentration of said first compound and said fourth concentration of said second compound are, independently, the same or different from said third concentration of said first compound and said third concentration of said second compound, respectively, withdrawing said modified second feedstream from said at least one chamber in this step (d), and passing said modified second feedstream to said first distributive valve, said second distributive valve, or a combination thereof;

e. recovering said modified first feedstream and said modified second feedstream;

f. providing at least one flush comprising a desorbent material to said first distributive valve, said second distributive valve, or a combination thereof;

g. contacting said modified adsorbent material from steps (c) and (d), simultaneously or step-wise, with said flush, whereby said first or said second compound is at least partially desorbed, to provide a modified flush; and h. passing said modified flush to said first distributive valve, said second distributive valve, or a combination thereof.

2. The process of claim 1, wherein said first compound is p-xylene and said second compound is selected from the group consisting of o-xylene, m-xylene, and ethylbenzene.

3. The process of claim 1, wherein step (c) and step (d) include the step of adsorbing o-xylene on said adsorbent material and wherein said first modified feedstream and said second modified feedstream comprise at least one compound selected from o-xylene, m-xylene, and ethylbenzene.

4. The process of claim 1, wherein said first feedstream in step (a) comprises at least one material selected from the group consisting of C8 aromatics, a mixture of olefins and paraffins, a mixture of normal paraffins, and fructose.

5. The process of claim 1, wherein said first feedstream in step (a) and said second feedstream in step (b) are independently selected from an equilibrium mixture of xylenes, a concentrated p-xylene stream from a selective toluene disproportionation unit, and filtrate from a crystallizer which is low in p-xylene.

6. The process of claim 1, wherein said second concentration of said first compound provided in step (a) is different from said first concentration of said first compound provided by step (b).

7. In an SMB process for separating a first compound in a feedstream from a mixture comprising a first compound and at least one other compound in said feedstream, the improvement comprising two distributive valves fluidly connected to each other and to plural adsorptive separation chambers, wherein each of said distributive valves has a separate source of feedstream, wherein said distributive valves process separate feedstreams having differing concentrations of said first compound.

8. In an SMB process using parallel rotary valves, the improvement comprising feeding a first feedstream to a first rotary valve and a second feedstream, different from said first feedstream, to a second rotary valve, and separating a predetermined product from each of said feedstreams without mixing of said feedstreams.

9. In an SMB process for separating a first compound in a feedstream from a mixture comprising a first compound and at least one other compound in said feedstream, the improvement comprising two distributive valves fluidly connected to each other and to plural adsorptive separation chambers, wherein each of said distributive valves has a source of at least one of a material selected from desorbent and flush, each of which is from a different source, whereby at least one of said plural adsorptive separation chambers is contacted with said mixture and then by said at least one of a material from each of said distributive valves.

* * * * *